United States Patent [19]
Eckerbom et al.

[11] Patent Number: 5,460,172
[45] Date of Patent: Oct. 24, 1995

[54] MOISTURE AND HEAT EXCHANGING UNIT FOR A RESPIRATION DEVICE

[75] Inventors: Anders Eckerbom, Bromma; Carl Hamilton, Kista; Robert Zyzanski, Gustavsberg, all of Sweden

[73] Assignee: Artema Medical AB, Sundbyberg, Sweden

[21] Appl. No.: 146,941

[22] Filed: Nov. 1, 1993

[51] Int. Cl.⁶ .................................................. A62B 18/08
[52] U.S. Cl. ............................. 128/201.13; 128/203.16; 128/205.12
[58] Field of Search .................... 55/DIG. 33, 498; 128/201.13, 203.16, 203.18, 203.26, 204.13, 205.12

[56] References Cited

U.S. PATENT DOCUMENTS

| | | | |
|---|---|---|---|
| 639,878 | 12/1899 | Wezel | 128/203.16 |
| 855,984 | 6/1907 | Russell | 128/204.13 |
| 3,002,870 | 10/1961 | Belgarde et al. | 55/498 |
| 3,815,754 | 6/1974 | Rosenberg | 55/497 |
| 4,036,616 | 7/1977 | Byrns | 55/498 |
| 4,063,913 | 12/1977 | Kippel et al. | 55/498 |
| 4,090,513 | 5/1978 | Togawa | 128/204.13 |
| 4,128,407 | 12/1978 | Chapel | 55/DIG. 33 |
| 4,327,717 | 5/1982 | Oetjen et al. | 128/204.13 |
| 4,516,573 | 5/1985 | Gedeon | 128/201.13 |
| 4,786,298 | 11/1988 | Billiet et al. | 55/498 |
| 4,798,676 | 1/1989 | Matkovich | 55/498 |
| 5,035,236 | 7/1991 | Kanegaonkar | 128/201.13 |
| 5,320,096 | 6/1994 | Hans | 128/201.13 |

FOREIGN PATENT DOCUMENTS

| | | | |
|---|---|---|---|
| 107636 | 1/1900 | Germany | 128/203.18 |
| 462367 | 6/1990 | Sweden | |
| 467685 | 8/1992 | Sweden | |

*Primary Examiner*—Edgar S. Burr
*Assistant Examiner*—Aaron J. Lewis
*Attorney, Agent, or Firm*—Jerry R. Seiler

[57] ABSTRACT

A moisture and heat exchanging unit for a respiration device such as a tracheal tube or tracheotomy canula, is described comprising a housing holding therein a moisture and heat exchanging body and/or a bacterial filter, said housing comprising two halves, a proximal half having an opening for connection with the airways of a patient and a distal half having an opening for communication with an air supply, said halves being mutually rotatable around a circular connection, one of said halves having an enlarged rim portion in locking, rotatable, relationship with a lid edge of the other of said halves. In a further embodiment, said halves are sealing against each other by an annular blade with tapering cross-section integral with one of said halves, sealing against an inclined internal surface of a collar integral with the other of said halves.

16 Claims, 2 Drawing Sheets

MOISTURE AND HEAT EXCHANGING UNIT FOR A RESPIRATION DEVICE

The present invention is related to a respiratory apparatus and in particular to a moisture and heat exchanging unit for a respiration device, such as a tracheal tube or tracheotomy canula.

BACKGROUND ART

A moisture and heat exchanging unit is employed for maintaining moisture and temperature of air, inhaled through a respiration device such as a tracheal tube or tracheotomy canula opening to ambient air or connected to a respirator, close to levels prevailing under normal breathing through the upper airways. Such unit also reduces the humidity of exhaled air, thus reducing condensation of water in tubes, respirator equipment etc. Moisture and heat exchanging units comprising a housing holding therein a porous structure impregnated with a hygroscopic compound are known in the art.

The traditional way of connecting respirator tubing to a patient involves the use of a Y-piece, a heat and moisture exchanger, a bacterial filter, a swivel and a flexible tube arrangement for stress-free connection to the patient tracheal tube, and also a T-piece adapter for connecting a gas analyzer sampling line.

The use of many different connecting components between the ventilator tubing and the patient in this way results in a bulky and space-demanding arrangement with a large dead space and many different connecting surfaces that are all potential air leaks. Normally, low cost swivel arrangements that do not include the use of separate sealing elements like O-rings are also associated with a certain "tolerable" leakage.

Although certain combination units are now available, e.g. filter-humidifier, humidifier with sampling port etc., in order to reduce the total number of connecting components, the use of several components tends to be expensive.

The abstract and drawings of SE-B-467685 discloses a device for moisturizing, heating and filtering of breathing air having one first opening connectible to a tracheal tube and at least one opening for inlet and outlet of air. A heat exchanging body is arranged within the device in such manner that the inhaled and exhaled air will pass therethrough via first and second surfaces, at least one of which being covered with a waved or folded filter for retaining bacteria and/or virus. In the embodiment shown, the apparatus has an oval cross-section with the inlet and outlet openings extending axially.

The abstract and drawings of SE-B-462367 discloses a breathing valve comprising a valve house holding a membrane and a filter. The house has an axial sleeve at one end. A heat exchanging shield with an inhalation channel in arranged at the opposite end of the housing, extending radially to enable pre-heating of the inhaled air by the patient's body heat.

Prior art devices are space-demanding, rigid and expensive. A more slim arrangement is desirable, provided that it can be made at low expense, with a minimum number of parts and with good sealing between the parts. A further demand is an adaptable design where inlet and outlet openings can be directed at different angles in relation to each other. However, devising an adaptable design is liable to encountering problems with loss of sealing capacity in the junction between the parts of the device. Many known sealing means such as O-rings or close fitting structures with exact dimensions are too expensive to be used in a disposable product.

DESCRIPTION OF THE INVENTION

The present invention is related to a moisture and heat exchanging unit for a respiration device, such as a tracheal tube or tracheotomy canula. An object of the invention is to provide a unit with two mutually rotatable parts sealingly connected to each other. A further object is to provide a simple and inexpensive unit that does not require a separate sealing element between the parts thereof. Further objects will be apparent from the following description. The invention fulfils the above objects and demands, in one embodiment, with a moisture and heat exchanging unit for a respiration device, comprising a housing holding therein a moisture and heat exchanging body and/or a bacterial filter, said housing comprising two halves, a proximal half having an opening for connection with the airways of a patient and a distal half having an opening for communication with an air supply, said halves being mutually rotatable around a circular connection, one of said halves having an enlarged rim portion in locking, rotatable, releasable relationship with a lid edge of the other of said halves. In a further embodiment, the invention is a moisture and heat exchanging unit for a respiration device, comprising a housing holding therein a moisture and heat exchanging body and/or a bacterial filter, said housing comprising two halves, a proximal half having an opening for connection with the airways of a patient and a distal half having an opening for communication with an air supply, said halves being mutually rotatable around a circular connection and sealing against each other by an annular blade with tapering cross-section integral with one of said halves, sealing against an inclined internal surface of a collar integral with the other of said halves. "Proximal" and "distal" are defined in relation to the patient.

The fact that the moisture and heat exchanging unit is defined as holding therein a moisture and heat exchanging body and/or a bacterial filter is due to the finding that many different structures can be employed while maintaining at least the basic requirements for the unit. Accordingly, the invention is applicable to a unit holding therein a moisture and heat exchanging body, a bacterial filter, or both. Thus, the bacterial filter is not always required, or its function can be concurrently fulfilled by the moisture and heat exchanging body and vice versa; and other parts, e.g. parts of the structure of the housing can help provide the function of the moisture and heat exchanging body.

The present invention allows several necessary functions to be integrated into one unit, and solves the problem of creating a tight seal between two rotatable halves of the device, without the use of any separate sealing elements. In this way, cost is reduced and a more safe and practical arrangement is achieved.

According to a preferred embodiment of the invention, the annular blade is arranged to seal against said inclined internal surface under pressure applied inside the housing.

According to a further preferred embodiment, the half integral with the annular blade of the moisture and heat exchanging unit of the invention is the distal half, and the half integral with the collar having the inclined inner surface is the proximal half.

According to another preferred embodiment of the invention, the openings are arranged as tubular conduits extending in a lateral direction on each of said halves, and preferably the distal half has two tubular conduits extending in a lateral direction, eliminating the need for a separate Y-piece.

DETAILED DESCRIPTION

Figure 1:
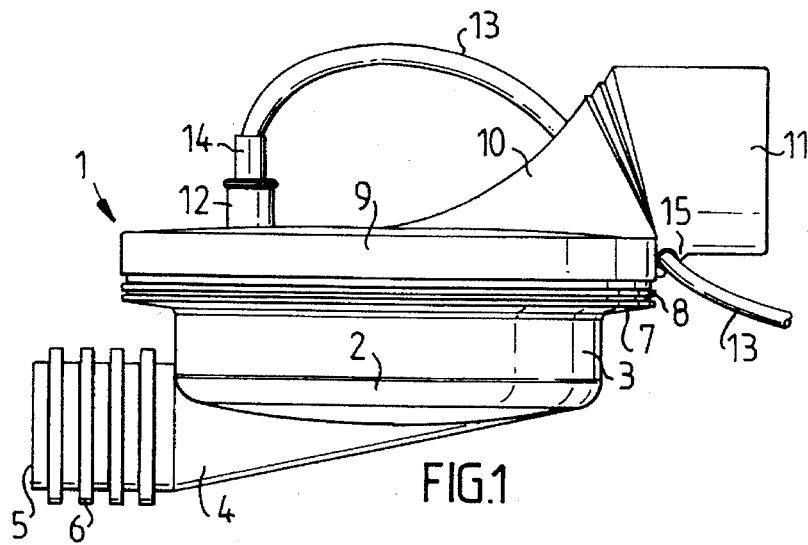
Figure 2:
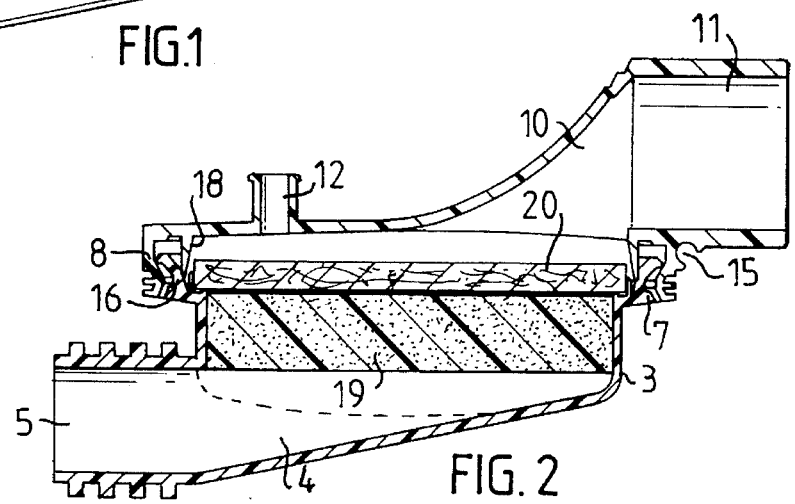
Figure 3B:
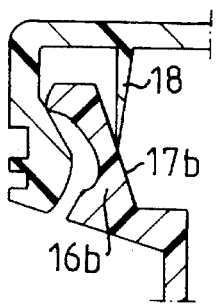
Figure 3C:
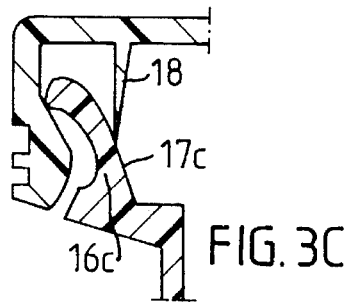
Figure 3A:
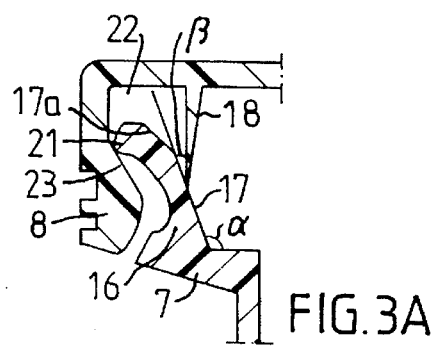
Figure 3D:
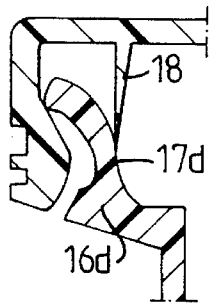
Figure 4:
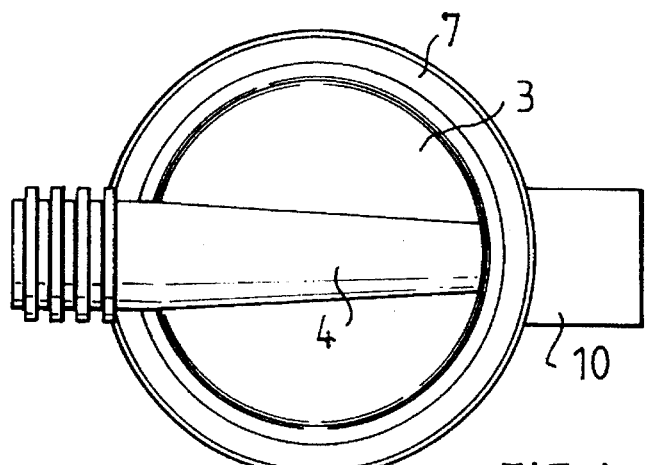
Figure 5:
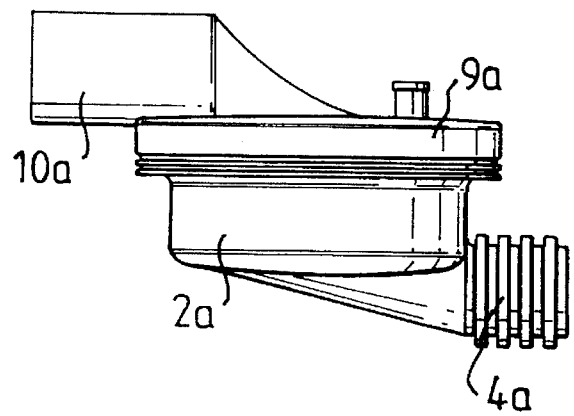
Figure 6:
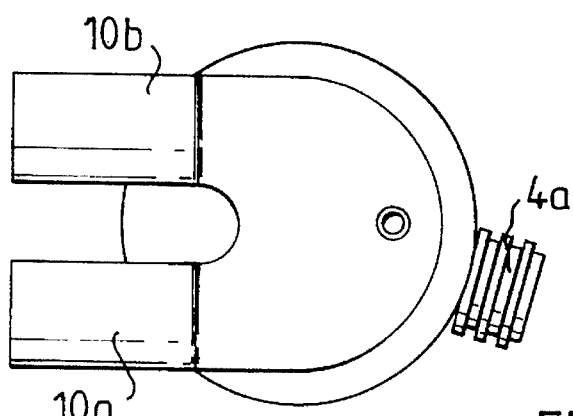

The invention is further described with reference to the enclosed drawings, without being limited by said drawings or the related description, wherein FIG. 1 is a side elevation of a device according to one preferred embodiment of the invention, FIG. 2 is a diametral section of the device in FIG. 1, FIG. 3a is a detail enlargement of sealing and locking means, substantially as appearing in FIG. 2, while FIGS. 3b, 3c and 3d are variants of FIG. 3a, FIG. 4 is a bottom view of the device in FIG. 1, FIG. 5 is a side elevation of a modified device according to one preferred embodiment of the invention, and FIG. 6 is a top view of the device in FIG. 5.

In the drawings, 1 represents a housing designed rather like a low cylinder comprising a lower, proximal half 2 including a cylindrical receptacle 3 carrying thereon a radial socket 4 projecting laterally into a cylindrical inlet 5 for connection of tubing for communication with the airways of a patient. Four grip flanges 6 are provided on the outer surface of the projecting part of socket 4. The lower half 2 has an enlarged rim portion 7 in locking, rotatable, releasable relationship with a lid edge 8 of an upper, distal, generally lid shaped upper half 9 of the housing 1. Another radial socket 10 on said lid projects laterally into an outlet 11, said outlet opening against the surrounding atmosphere or being connected to a respirator, anaesthesia apparatus or the like. A Y-piece may be connected to the outlet, to provide, with appropriate valves, separate channels for exhaled and inhaled air. Upper half 9 has a further socket 12, extending from the top surface thereof, for optional connection with a sampling tubing 13 introduced therein via an appropriate plunger 14. A grip 15 for the tubing is shaped integral with the upper half and its outlet socket. When the optional connection is not used, socket 12 is closed with an appropriate stopper. As apparent from FIG. 2, and in more detail in FIG. 3a, the rim 7 of the lower half has an inwardly extending circular collar 16. The inner surface 17 thereof is inclined or slanted at least at a portion thereof, and an annular blade 18 with an elongated tapering cross-section extends inwardly from and is integral with the upper part and is biased at its edge in a wiper-like manner against said inclined surface. Sealing will be effective by the inclined surface or portion exerting a radial force on the annular blade. Air pressure applied within the unit, e.g. from a respiration apparatus, will make the annular blade tighten against the inclined surface.

Inside the lower half, a moisture and heat exchanging body 19 fills out the cylindrical receptacle 3, in such way that exhaled and inhaled air will pass therethrough, body 19 thus acting as a regenerating exchanger for heat and moisture, i.e. mimicking the human upper airways. On top of body 19, i.e. on the "dry and cold" side thereof, a bacterial filter 20 is positioned to filter exhaled and inhaled air.

The orientation of the inclined inner surface as well as the angle at which the annular blade abuts said surface were found to be important, although variation must be provided to take into account different sizes and materials. The angle $\alpha$ is in most cases between 95° and 160° and preferably between 105° and 135°, while being about 110° in the design illustrated in FIG. 3a. The angle $\beta$, at which the annular blade abuts the inclined surface is acute and is in most cases between 5° and 70° and preferably between 10° and 45°, while being about 20° in the design illustrated in FIG. 3a. A portion 17a of the inclined surface has a greater angle in order to facilitate the introduction of the annular blade.

In FIGS. 3b through 3d the collars 16b through 16d have a different design, the inclined surface being straight as 17b, curved as 17c or S-curved as 17d.

The locking, rotatable, releasable relationship of the enlarged rim portion 7 with the lid edge 8 is brought about by an annular flange 21 extending from the circular collar 16 into and in rotatable engagement with the lid edge 8 in an annular recess 22 formed between the lid edge 8 and the annular blade 18 said annular flange 21 exerting force within said recess 22 against an inward surface 23 of the lid edge 8, thus providing a snap function securing the distal and proximal parts to each other and furthermore forcing the slanted surface 17 against the outer edge of the annular blade 18 thus securing a gas tight seal between said slanted surface and said annular blade.

The modified device of FIGS. 5 and 6 is similar to the device in FIG. 1, except for having in the distal half 9a two parallel sockets 10a and 10b for inhaled and exhaled air, respectively, thus eliminating the need for a separate Y-piece. The socket 4a in the proximal half 2a is shown rotated about 165° from sockets 10a and 10b.

Materials for the upper part, i.e. the part having the annular blade integral therewith is a somewhat flexible polymer material, also providing low friction. The hardness of the material is bound by limitations, not necessarily being critical but being preferred in the embodiments disclosed in the drawings. A too soft material will deteriorate the snap function, possibly causing inadvertent disassembly of the halves. A too hard material on the other hand may deteriorate the sealing function of the annular blade by causing insufficient resilience of the blade edge and obstructing assembly of the halves. In situations where there is a conflict in hardness requirements within the upper part, a double-cast upper half may be employed wherein the annular blade or the edge thereof is cast from softer material than the rest of the upper half. A preferred hardness interval for the part having the annular blade is 70 Shore A to 65 Shore D, more preferably 45 Shore D to 55 Shore D. Particularly suitable materials are polyolefins or fluorinated polyolefins such as polytetrafluorethene (PTFE) Teflon™, low density polyethene (LDPE), high density polyethene (HDPE) and polypropene. The upper part need not be weldable.

For the lower part, i.e. the part having the inclined surface, a fairly stiff weldable material is preferred, e.g. polymethylmetacrylate (PMMA) or polycarbonate (PC). Like with the upper part, a too soft material may cause the parts to engage too loosely. Furthermore, the inclined internal circular surface should be harder than the edge of the annular blade to achieve the required gas tight sealing. Accordingly a hardness greater than 65 Shore D is preferred for the part having the inclined surface.

The insert material, i.e. the material for the moisture and heat exchanging body is in a preferred example an open cell polyurethane foam impregnated with a hygroscopic salt, preferably LiCl, $CaCl_2$ or $MgCl_2$.

The bacterial filter sealed to the lower part by welding along its periphery, is an open structure felt-like material, preferably made up of synthetic fibres which have a permanent electrostatic polarization. Particles are attracted to the fibres and kept in the filter by the active electrostatic forces.

This type of filter material has a relatively large pore size resulting in low resistance to air flow.

We claim:

1. A moisture and heat exchanging unit for a respiration device, comprising a housing holding therein a moisture and heat exchanging body and/or a bacterial filter, said housing comprising first and second halves, a proximal half having an opening for connection with the airways of a patient and a distal half having an opening for communication with an air supply, said first half having an annular recess extending therearound said annular recess defined between an interior circular surface and an annular blade, said second half having an annular flange extending therearound, said annular flange extending into said annular recess and urged against said interior surface thereof to form a circular rotatable connection therewith and wherein said annular blade is urged against said annular flange and forms a rotatable gas-tight seal thereagainst, and whereby said halves are mutually rotatable around said circular connection.

2. A unit as defined in claim 1 wherein said annular blade has a tapering cross-section.

3. A unit as defined in claim 1 wherein said gas-tight seal is tightened under pressure applied inside the housing.

4. A unit as defined in claim 1, wherein the first half is the distal half, and the second half is the proximal half.

5. A unit as defined in claim 1, wherein the openings are arranged as tubular conduits extending in a lateral direction on each of said halves.

6. A unit as defined in claim 5, wherein the distal half has two tubular conduits extending in a lateral direction, eliminating the need for a separate Y-piece.

7. A unit as defined in claim 1 wherein said annular flange comprises a substantially rigid projection in rotatable forcible engagement with said interior surface of said annular recess.

8. A unit as defined in claim 7 wherein said annular flange has an inclined circular surface engaging said annular blade to form said gas tight seal therebetween.

9. A respiratory apparatus having a housing containing a heat and moisture exchange device and/or a bacteria filter, said housing comprising:

a first and a second component in a rotatable gas-sealing engagement, said first component having an integral annular blade extending therein and having a concentric annular recess formed therein;

said second component having an inclined circular surface for engaging said annular blade and forming a gas tight seal thereagainst, and having an annular flange extending into said annular recess and in rotatable engagement therein for urging said inclined circular surface against said annular blade to form a rotatable gas tight seal therebetween.

10. The apparatus of claim 9 wherein said annular blade includes a flexible, memory-retaining annular surface for sealingly engaging said inclined circular surface.

11. The apparatus of claim 9 wherein said annular flange comprises a substantially rigid projection extending from said inclined surface and forcibly engages a surface of said annular recess.

12. The apparatus of claim 9 wherein said annular flange is in rotatable and locking engagement within said annular recess.

13. The apparatus of claim 9, wherein said annular flange in rotatable engagement in said annular recess causes said annular blade to tighten against said inclined circular surface under pressure applied inside the housing.

14. The apparatus of claim 9, wherein the component integral with said annular blade is distal, and the component having an inclined circular surface is proximal in relation to a patient connected to the apparatus.

15. The apparatus of claim 9, wherein tubular conduits are arranged extending in a lateral direction on each of said first and second components for connection with the airways of a patient and for communication with an air supply, respectively.

16. The apparatus of claim 15, wherein the component for communication with an air supply, has two tubular conduits extending in a lateral direction, eliminating the need for a separate Y-piece.

* * * * *